United States Patent [19]

Garabedian

[11] Patent Number: Plant 7,082

[45] Date of Patent: Dec. 26, 1989

[54] PLUM TREE, RANCHO OCHO

[76] Inventor: John M. Garabedian, P.O. Box 7883, Fresno, Calif. 93747

[21] Appl. No.: 268,348

[22] Filed: Nov. 7, 1988

[51] Int. Cl.[4] ..... A01H 5/00

[52] U.S. Cl. ..... Plt./38

[58] Field of Search ..... Plt. 38

*Primary Examiner*—Robert E. Bagwill

*Attorney, Agent, or Firm*—Worrel & Worrel

[57] ABSTRACT

A new and distinct variety of plum tree which is characterized as to novelty by producing semi-freestone fruit which are ripe for harvesting and shipment approximately June 20 through June 26 under the ecological conditions prevailing at Fresno, Calif. in the San Joaquin Valley of central California.

1 Drawing Sheet

BACKGROUND OF THE NEW VARIETY

The present invention relates to a new and distinct variety of Plum Tree hereinafter denominated varietally as "Rancho Ocho" and more particularly to a novel plum tree which produces fruit which have a somewhat similar external appearance as compared with the fruit produced by the Santa Rosa-Two Plum Tree (U.S. Plant Pat. No. 5,904), but which is distinguished therefrom and characterized principally as to novelty, by producing fruit which are ripe for commercial harvesting and shipment approximately June 20 through June 26 in Fresno, Calif., and which further produces fruit which are semi-freestone by nature in contrast to the Santa Rosa-Two Plum Tree which produces a clingstone fruit.

The Santa Rosa-Two variety of plum tree (U.S. Plant Pat. No. 5,904) is known as a vigorous producer of medium to large fruit which are ripe for harvesting and shipment approximately five days before the Santa Rosa Plum Tree (unpatented) in the San Joaquin Valley of central California. Heretofore the Santa Rosa Plum Tree was probably considered the most important variety of plum tree grown in the San Joaquin Valley from the standpoint of both commercial and home use. In contrast to the Santa Rosa Plum Tree, the Santa Rosa-Two Plum Tree has come to be known for its production of fruit which have an attractive purplish-red skin color, an amber flesh color, and a noteworthy flavor.

The inventor has for decades cross-pollinated various varieties of fruit trees having known desirable characteristics in an attempt to produce new varieties of fruit trees which bear crops that individually have dates for commercial harvesting and shipment which are somewhat later than those varieties which they are most closely similar. These activities have been undertaken in an effort to bring fruit to market at a time when similar varieties were not commercially available.

In this regard, the applicant, in 1973, discovered within the cultivated area of his Ranch No. 1, which is located at the corner of Fowler and Kings Canyon Avenues, Fresno, Calif., a chance open-pollinated seedling of unknown parentage. The applicant noted the desirable characteristics of this new and novel variety of plum tree and subsequently marked the chance seedling for future observation.

ORIGIN AND ASEXUAL REPRODUCTION OF THE NEW VARIETY

The present variety of plum tree was an open-pollinated seedling of unknown parentage which was discovered within the cultivated area of the applicant's Ranch No. 1 which is located on the corner of Fowler and Kings Canyon Avenues, in Fresno, Calif. in 1973. The subject variety was observed at that time to have desirable characteristics and the inventor subsequently asexually reproduced the subject variety by removing buds, in 1974, and then in 1975, from the seedling and by budding them into test seedlings which were then growing on applicant's Ranch No. 8 which is located on the corners of Belmont and Armstrong Avenues in Fresno County, Calif. These budded test seedlings have been continually observed and evaluated by the inventor and it has subsequently been determined that the progeny produced by this first asexual reproduction technique possess the same distinctive characteristics as that shown in the original open-pollinated seedling.

SUMMARY OF THE NEW VARIETY

The Rancho Ocho Plum Tree of the present invention is noteworthy in producing semi-freestone fruit which are ripe for commercial harvesting and shipment approximately June 20 through June 26 under the ecological conditions prevailing in Fresno, Calif. The subject variety is mature for harvesting and shipment approximately in the same season as the Santa Rosa-Two Plum Tree (U.S. Plant Pat. No. 5,904) at the same geographical location.

BRIEF DESCRIPTION OF THE DRAWINGS

The accompanying drawing is an illustration by photographic reproduction of a twig bearing typical leaves showing the top and bottom surface colors thereof, several fruit of the subject variety sufficiently matured for harvesting and shipment, two fruit halved in the axial plane to show the flesh characteristics thereof and two stones, all of the subject variety.

DETAILED DESCRIPTION

Referring more specifically to the pomological details of this new and distinct variety of Plum Tree, the following has been observed under the ecological conditions prevailing at the orchard of the inventor which is located at the corner of Belmont and Armstrong Avenues in Fresno, Fresno County, Calif. All major color code designations are by reference to the Dictionary of Color, Second Edition, by Maerz and Paul, published in 1950. Common color names are also employed occasionally.

TREE

Size:
*Generally.*—Large as compared with other plum cultivars common to the San Joaquin Valley of central California.
Vigor: Vigorous.
Figure: Upright, open, vase formed and tender, depending upon pruning practices.
Productivity: Productive.
Regularity of bearing: Regular.
Trunk:
*Size.*—Stocky.
*Surface texture.*—Shaggy.
Branches:
*Size.*—Average.
*Surface texture.*—Shaggy.
*Color.*—A dull brown. The color of the branches is not particularly distinctive of the subject variety, however.
Lenticels:
*Numbers.*—Average.
*Size.*—Small.

LEAVES

Size:
*Generally.*—Medium to large.
*Average length.*—Approximately 11.5 cm.
*Average width.*—Approximately 5.2 cm.
*Size — Generally.*—Variable, elliptical and occasionally ovate; acutely pointed.
Leaf apex:
*Shape.*—Acuminate.
Leaf base:
*Shape.*—Acute.
Thickness:
*Generally.*—Average.
Color:
*Upwardly disposed surfaces.*—Dark green, (Plate 28, E-8, Page 69).
*Downwardly disposed surfaces.*—Pale green (Plate 22, I-5, Page 67).
Surface texture: Glabrous.
Marginal form: Finely serrate.
Petiole:
*Size.*—Average.
*Average length.*—Approximately 13.7 mm.
*Thickness.*—Slender, approximately 1.8 mm.
Glands:
*Generally.*—Not readily visible.

FLOWER BUDS

Generally: The flower buds are considered to be small and tender as compared with other common plum cultivars.
Shape:
*Generally.*—Short, pointed, and free.
Pubescent: The variety is only minimally pubescent.

FLOWERS

Date of first bloom: In 1987, first bloom was observed on February 25.
Date of full bloom: In 1987, full bloom was observed on March 6.
Date of bloom:
*Generally.*—Average as compared with other common plum cultivars growing in the San Joaquin Valley of central California.
Size:
*Generally.*—Small.
Petals:
*Color.*—White.
Flowers produced per node:
*Generally.*—The flowers are produced at each node.
Pollen:
*Color.*—Light yellow.
Anthers:
*Color.*—A light cream color; this color is not particularly distinctive of the subject variety, however.

FRUIT

Maturity when described: In 1987, the variety was ripe for commercial harvesting and shipment approximately June 20 through June 26 in Fresno, Calif.
Size:
Generally.—Uniformly large.
*Average axial diameter.*—Approximately 55.2 mm.
*Average diameter transverse and in the suture plane.*—Approximately 57.2 mm.
*Average diameter transverse and at right angles to the suture plane.*—Approximately 55.6 mm.
Form:
*Uniformity.*—Symmetrical.
Shape:
*Generally.*—Rounded.
Suture:
*Generally.*—The suture appears as an inconspicuous and very shallow line which extends from the base to the pistil point. The suture discontinues at the pistil point.
Ventral surface:
*Shape.*—Rounded.
Stem cavity:
*Shape.*—Elongated in the suture plane.
*Depth.*—Approximately 8.6 mm.
*Width.*—Approximately 11.8 mm.
Base:
*Shape.*—Rounded.
Apex:
*Shape.*—Rounded.
Pistil point:
*Location.*—Apical.
Skin:
*Thickness.*—Considered medium to thin.
*Surface texture.*—Glabrous and tender.
Tenacious to flesh: Yes.
Tendency to crack: Not observed in the dry season.
Skin:
*Color.*—A dark red, (Plate 48, J-12).
Down:
*Quantity.*—Wanting.
Flesh:
*Color.*—The subject variety has a light reddish tinge throughout. The intensity of the flesh coloration increases with senescence, (Plate 7, J-6).
Surface of pit cavity:
*Color.*—Red. This color is quite similar to the flesh color.

Amygdalin:
*Quantity.*—Scant.
Juice production: Average as compared with other plum cultivars.
Texture: Average; soft and fine. The variety is considered to have a melting flesh texture at full commercial maturity.
Fibers:
*Numbers.*—Few.
*Texture.*—Fine.
Ripening: Even.
Flavor:
*Generally.*—Considered mild to subacid.
Aroma: Wanting.
Eating quality:
*Generally.*—Good.

STONE

Attachment: The subject variety is considered semi-freestone by nature. More particularly, the stone of the instant variety adheres to the flesh along its ventral edge.
Fibers:
*Length.*—Short. The stone remains short fiber-like threads along its ventral edge.
Color:
*Generally.*—Light brown, (Plate 10, C-7, Page 43).
Size:
*Generally.*—Average.
*Average length.*—Approximately 22.2 mm.
*Average width.*—Approximately 18.2 mm.
*Average thickness.*—Approximately 11.6 mm.
Form:
*Generally.*—Variable, considered oval although occasionally ovoid-type stones may be observed.
Base:
*Shape.*—Straight.
Apex:
*Shape.*—Acuminate.
Sides:

*Generally.*—Unequal and appearing slightly flattened. Further the sides appear curved.
Surface texture:
*Generally.*—Irregularly furrowed. Further a distinct ridge appears on the ventral side.
Ridges:
*Shape.*—Rounded.
Ventral edge: Thick.
Dorsal edge: Narrow and shallow.
Use: The new variety of Plum Tree produces a fresh market type plum.
Storage quality: Average.
Resistance to insects and disease: Considered average as compared with other common plum cultivars.
Shipping quality: Average.

Although the new variety of plum tree possesses the described characteristics when grown under the ecological conditions prevailing in Fresno, Fresno County, Calif., in the central part of the San Joaquin Valley of California, it is to be understood that variations of the usual magnitude and characteristics incident to changes in growing conditions, fertilization, pruning and pest control are to be expected.

Having thus described and illustrated my new variety of plum tree, what is claimed as new and desired to be secured by Letters Patent is:

1. A new and distinct variety of plum tree substantially as illustrated and described and which is denominated varietally by the name "Rancho Ocho", the new variety of plum tree being somewhat similar to the Santa Rosa-Two Plum Tree (U.S. Plant Pat. No. 5,904) which matures at approximately the same time of the season, but from which it is distinguished therefrom, and characterized principally as to novelty, by bearing semi-freestone fruit which are ripe for commercial harvesting and shipment approximately June 20 through June 26 under the ecological conditions prevailing at Fresno, Calif.

* * * * *

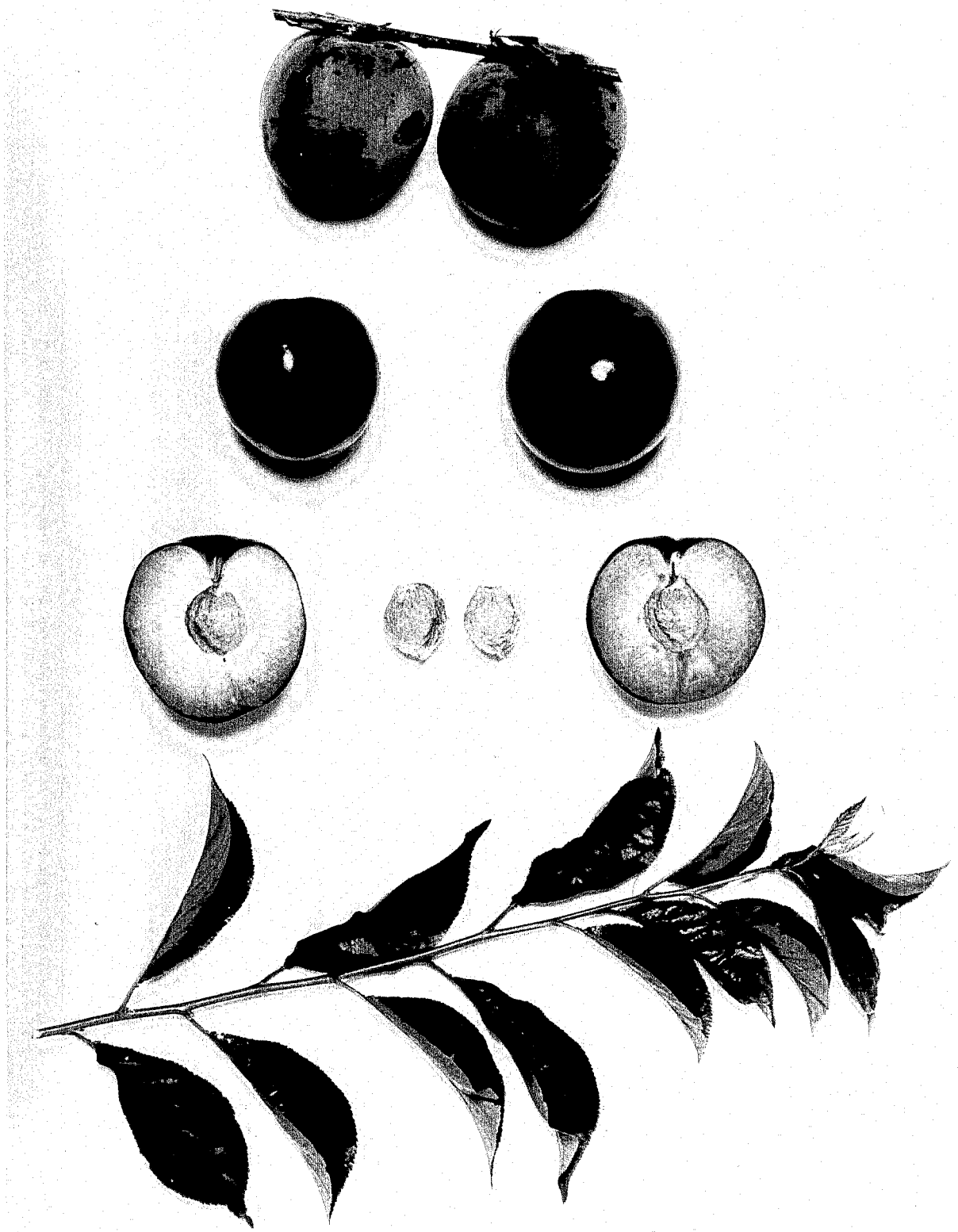

UNITED STATES PATENT AND TRADEMARK OFFICE

CERTIFICATE OF CORRECTION

PATENT NO. : PP. 7,082

DATED : Dec. 26, 1989

INVENTOR(S) : John M. Garabedian

It is certified that error appears in the above-identified patent and that said Letters Patent is hereby corrected as shown below:

Column 4, Line 12

Delete "The", and Insert ---Two---

Column 5, Line 24

Delete "remains", and insert ---retains---

Signed and Sealed this

Seventeenth Day of December, 1991

*Attest:*

*Attesting Officer*

HARRY F. MANBECK, JR.

*Commissioner of Patents and Trademarks*